US008891781B2

(12) United States Patent
Ohta et al.

(10) Patent No.: US 8,891,781 B2
(45) Date of Patent: Nov. 18, 2014

(54) ACTIVE VIBRATION NOISE CONTROL DEVICE

(75) Inventors: Yoshiki Ohta, Sakado (JP); Yoshitomo Imanishi, Fujimi (JP); Tomomi Hasegawa, Kawasaki (JE); Manabu Nohara, Turugashima (JP); Yusuke Soga, Kawasaki (JP)

(73) Assignee: Pioneer Corporation, Kanagawa (JP)

( * ) Notice: Subject to any disclaimer, the term of this patent is extended or adjusted under 35 U.S.C. 154(b) by 479 days.

(21) Appl. No.: 13/264,065

(22) PCT Filed: Apr. 15, 2009

(86) PCT No.: PCT/JP2009/057592
§ 371 (c)(1), (2), (4) Date: Oct. 12, 2011

(87) PCT Pub. No.: WO2010/119528
PCT Pub. Date: Oct. 21, 2010

(65) Prior Publication Data
US 2012/0033821 A1 Feb. 9, 2012

(51) Int. Cl.

| | |
|---|---|
| ***G10K 11/16*** | (2006.01) |
| ***G10K 11/178*** | (2006.01) |
| *A61F 11/06* | (2006.01) |
| *H04S 7/00* | (2006.01) |

(52) U.S. Cl.
CPC ........ *G10K 11/1782* (2013.01); *H04R 2499/13* (2013.01); *H04S 7/301* (2013.01)
USPC ........................................ 381/71.4; 381/71.1

(58) Field of Classification Search
CPC .................... G10K 11/178; G10K 2210/1282; H04R 1/1083; H04R 2499/13
USPC ............. 381/71.1–71.12, 94.1–94.9, 97, 302
See application file for complete search history.

(56) References Cited

U.S. PATENT DOCUMENTS

| | | | | |
|---|---|---|---|---|
| 2005/0053244 | A1* | 3/2005 | Onishi et al. | ............... 381/71.11 |
| 2007/0038441 | A1 | 2/2007 | Inoue et al. | |

FOREIGN PATENT DOCUMENTS

| | | |
|---|---|---|
| JP | 03-153927 | 7/1991 |
| JP | 07-168582 | 7/1995 |
| JP | 07-199969 | 8/1995 |
| JP | 09-093087 | 4/1997 |
| JP | 2006-038136 | 2/2006 |
| JP | 2007-047367 | 2/2007 |
| JP | 2007-272008 | 10/2007 |

OTHER PUBLICATIONS

International Search Report, PCT/JP2009/057592, Jun. 23, 2009.

* cited by examiner

*Primary Examiner* — Vivian Chin
*Assistant Examiner* — Ammar Hamid
(74) *Attorney, Agent, or Firm* — Young & Thompson

(57) ABSTRACT

An active vibration noise control device having a pair of speakers, including: a basic signal generating unit generating a basic signal based on a vibration noise frequency; an adaptive notch filter generating a first control signal provided to one speaker using a first filter coefficient and generating a second control signal provided to the other speaker using a second filter coefficient to cancel the generated vibration noise; a microphone detecting cancellation error between the vibration noise and the control sounds and outputting an error signal; a reference signal generating unit generating a reference signal based on a transfer function from the speakers to the microphone; a filter coefficient updating unit updating first and second filter coefficients, minimize the error signal; and a phase difference limiting unit limiting a phase difference between control sounds generated by different speakers. Therefore, it becomes possible to appropriately ensure a uniform and wide noise-cancelled area.

7 Claims, 11 Drawing Sheets

ACTIVE VIBRATION NOISE CONTROL DEVICE

TECHNICAL FIELD

The present invention relates to a technical field for actively controlling a vibration noise by using an adaptive notch filter.

BACKGROUND TECHNIQUE

Conventionally, there is proposed an active vibration noise control device for controlling an engine sound heard in a vehicle interior by a controlled sound output from a speaker so as to decrease the engine sound at a position of passenger's ear. For example, noticing that a vibration noise in a vehicle interior is generated in synchronization with a revolution of an output axis of an engine, there is proposed a technique for cancelling the noise in the vehicle interior on the basis of the revolution of the output axis of the engine by using an adaptive notch filter so that the vehicle interior becomes silent, in Patent Reference-1. The adaptive notch filter is a filter based on an adaptive control.

There are disclosed techniques related to the present invention in Patent Reference 2 and Non-Patent Reference 1.

PRIOR ART REFERENCE

Patent Reference

Patent Reference-1: Japanese Patent Application Laid-open under No. 2006-38136

Patent Reference-2: Japanese Patent Application Laid-open under No. 03-153927

Non-Patent Reference

Non-Patent Reference 1: Kazuo Ito and Hareo Hamada, "Active control of noise and vibration using single-frequency adaptive notch filter", TECHNICAL REPORT OF IEICE, EA93-100 (1994-03)

DISCLOSURE OF INVENTION

Problem to be Solved by the Invention

However, since the above techniques perform an optimization so as to minimize an error at a microphone point, there is a case that the vibration noise increases at a position other than the microphone point and an un-uniform noise-cancelled area occurs.

The present invention has been achieved in order to solve the above problem. It is an object of the present invention to provide an active vibration noise control device which can appropriately suppress an occurrence of an un-uniform noise-cancelled area and ensure a wide noise-cancelled area.

Means for Solving the Problem

In the invention according to claim 1, an active vibration noise control device having a pair of speakers which makes the speakers generate control sounds, includes: a basic signal generating unit which generates a basic signal based on a vibration noise frequency generated by a vibration noise source; an adaptive notch filter which generates a first control signal provided to one of the speakers by applying a first filter coefficient to the basic signal and generates a second control signal provided to the other speaker by applying a second filter coefficient to the basic signal, in order to make the speakers generate the control sounds so that the vibration noise generated by the vibration noise source is cancelled; a microphone which detects a cancellation error between the vibration noise and the control sounds and outputs an error signal; a reference signal generating unit which generates a reference signal from the basic signal based on a transfer function from the speakers to the microphone; a filter coefficient updating unit which updates the first and second filter coefficients used by the adaptive notch filter based on the error signal and the reference signal so as to minimize the error signal; and a phase difference limiting unit which limits a phase difference between a control sound generated by one of the speakers and a control sound generated by the other speaker.

DETAILED DESCRIPTION OF THE PREFERRED EMBODIMENTS

Figure 1:
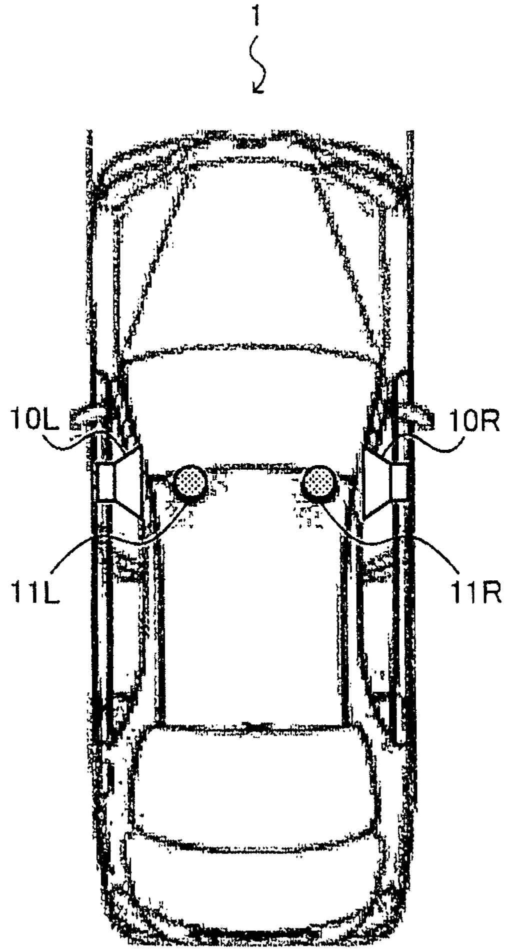
FIG. 1 is a diagram for explaining an arrangement example of speakers and microphones in an active vibration noise control device.

According to one aspect of the present invention, there is provided an active vibration noise control device having a pair of speakers which makes the speakers generate control sounds, including: a basic signal generating unit which generates a basic signal based on a vibration noise frequency generated by a vibration noise source; an adaptive notch filter which generates a first control signal provided to one of the speakers by applying a first filter coefficient to the basic signal and generates a second control signal provided to the other speaker by applying a second filter coefficient to the basic signal, in order to make the speakers generate the control sounds so that the vibration noise generated by the vibration noise source is cancelled; a microphone which detects a cancellation error between the vibration noise and the control sounds and outputs an error signal; a reference signal generating unit which generates a reference signal from the basic signal based on a transfer function from the speakers to the microphone; a filter coefficient updating unit which updates the first and second filter coefficients used by the adaptive notch filter based on the error signal and the reference signal so as to minimize the error signal; and a phase difference limiting unit which limits a phase difference between a control sound generated by one of the speakers and a control sound generated by the other speaker.

The above active vibration noise control device having a pair of speakers is preferably used for cancelling the vibration noise from the vibration noise source by making the speakers generate the control sounds. The basic signal generating unit generates the basic signal based on the vibration noise frequency generated by the vibration noise source. The adaptive notch filter generates the first control signal provided to one of the speakers by applying the first filter coefficient to the basic signal and generates the second control signal provided to the other speaker by applying the second filter coefficient to the basic signal. The microphone detects the cancellation error between the vibration noise and the control sounds and outputs the error signal. The reference signal generating unit generates the reference signal from the basic signal based on the transfer function from the speakers to the microphone. The filter coefficient updating unit updates the first and second filter coefficients used by the adaptive notch filter so as to minimize the error signal. The phase difference limiting unit limits the phase difference between the control sound generated by one of the speakers and the control sound generated by the other speaker.

By the above active vibration noise control device, it is possible to appropriately suppress the occurrence of the un-uniform noise-cancelled area. Therefore, it becomes possible to appropriately ensure the uniform and wide noise-cancelled area. Additionally, since it is possible to suppress the increase in the amplitudes of the control sounds by limiting the phase difference, it becomes possible to ensure the wide noise-cancelled area by the relatively small volume of the control sounds.

In a manner of the above active vibration noise control device, the phase difference limiting unit limits the phase difference so that a sound pressure distribution generated by the control sounds from the speakers becomes uniform. Namely, the phase difference limiting unit can limit the phase difference so that the deviation of the sound pressure distribution generated by the two speakers does not occur.

In another manner of the above active vibration noise control device, the phase difference limiting unit limits an angular difference on a two-dimensional plane between the first and second filter coefficients updated by the filter coefficient updating unit, to a predetermined angle or less, so as to limit the phase difference between the control sound generated by one of the speakers and the control sound generated by the other speaker. Therefore, it becomes possible to appropriately limit the phase difference between the control sounds from the speakers.

In a preferred example of the above active vibration noise control device, when the angular difference is larger than the predetermined angle, the phase difference limiting unit can provide the adaptive notch filter with the first and second filter coefficients before the update by the filter coefficient updating unit.

In another manner of the above active vibration noise control device, the phase difference limiting unit limits a phase difference between the first and second control signals generated by the adaptive notch filter, to a predetermined value or less, so as to limit the phase difference between the control sound generated by one of the speakers and the control sound generated by the other speaker. Therefore, it becomes possible to appropriately limit the phase difference between the control sounds from the speakers, too.

In a preferred example of the above active vibration noise control device, when the phase difference is larger than the predetermined value, the phase difference limiting unit can delay one of the first and second control signals, a phase of which is more advanced than that of the other, by amount corresponding to a difference between the phase difference and the predetermined value.

Preferably, the speakers are arranged close to the vibration noise source. For example, the speakers are installed on the front side in the vehicle interior. Therefore, it becomes possible to effectively cancel the vibration noise from the vibration noise source.

EMBODIMENT

Preferred embodiments of the present invention will be explained hereinafter with reference to the drawings.

[Basic Concept]

First, a description will be given of a basic concept of the present invention. As shown in FIG. 1, such an example that an active vibration noise control device mounted on a vehicle 1 which includes two speakers 10L and 10R and two microphones 11L and 11R will be given. The speakers 10L and 10R and the microphones 11L and 11R are installed on the front side in the vehicle interior. For example, the speakers 10L and 10R are installed in the front doors. Additionally, the speakers 10L and 10R are formed in pairs.

Here, a description will be given of a problem of a conventional active vibration noise control device, with reference to FIG. 2, FIGS. 3A and 3B and FIGS. 4A and 4B. The active vibration noise control device makes the speakers generate the control sounds based on the frequency in accordance with the revolution of the engine output axis so as to actively control the vibration noise of the engine as the vibration noise source. Concretely, the active vibration noise control device feeds back the error signal detected by the microphone and minimizes the error by using the adaptive notch filter so as to actively control the vibration noise. Basically, the conventional active vibration noise control device performs the optimization so as to minimize the error at the microphone point.

Figure 2:
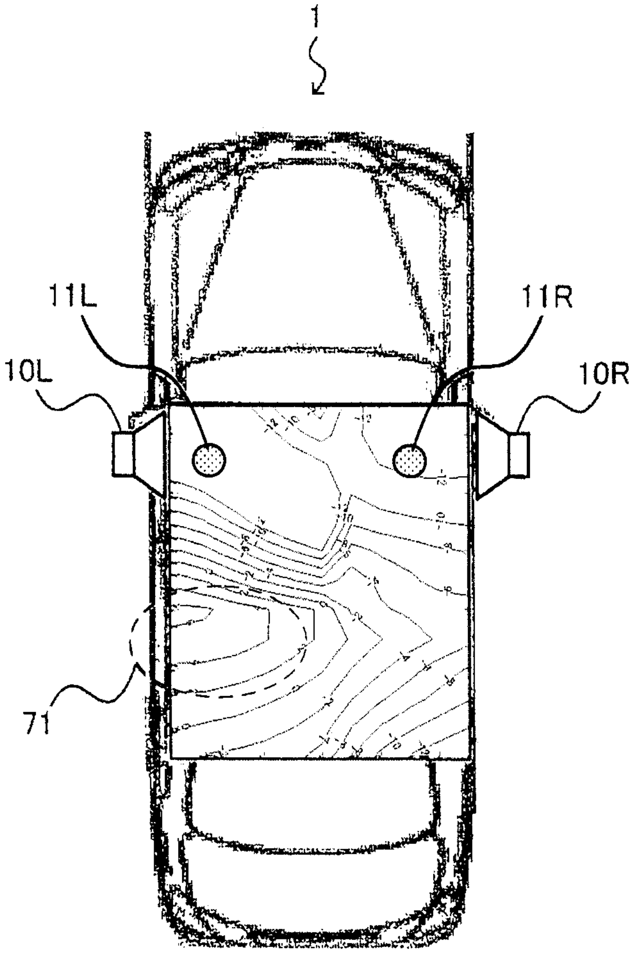
FIG. 2 is a diagram for explaining a problem of a conventional active vibration noise control device.

FIG. 2 is a diagram for explaining a problem of the conventional active vibration noise control device. FIG. 2 shows an example of a sound pressure distribution in the vehicle interior when the conventional active vibration noise control device makes the speakers 10L and 10R generate the control sounds so as to actively control the vibration noise of the engine. As shown by an area drawn in a broken line 71, it can be understood that the vibration noise increases at the position other than the microphone point and the un-uniform noise-cancelled area occurs. Concretely, it can be understood that the vibration noise increases at the position of the left rear seat.

Next, a description will be given of a reason for the occurrence of the un-uniform noise-cancelled area as shown in FIG. 2, with reference to FIGS. 3A and 3B and FIGS. 4A and 4B.

Figure 3A:
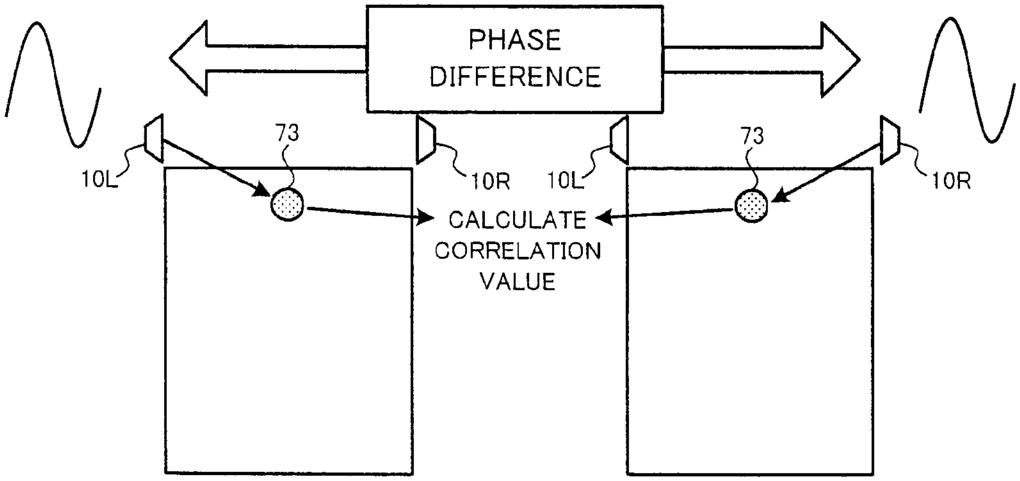
FIGS. 3A and 3B are diagrams for explaining a phase difference between speakers.
Figure 3B:
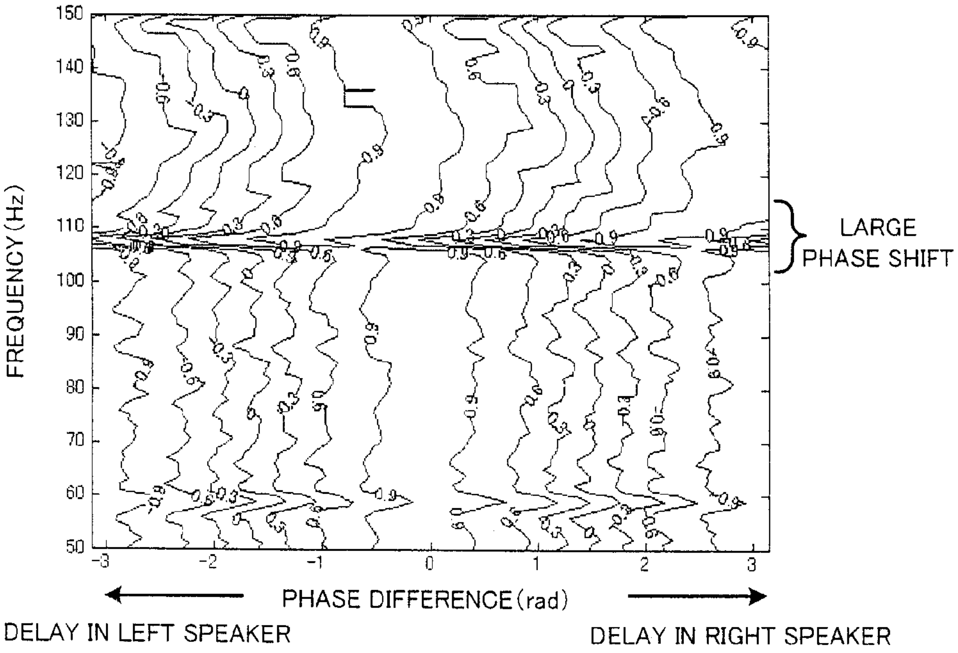

FIGS. 3A and 3B are diagrams for explaining a concrete example of a phase difference between the speakers 10L and 10R. Here, as shown in FIG. 3A, it is assumed that control sounds (sine waves) generated by the left speaker 10L and the right speaker 10R are separately recorded by a microphone located at a center position 73 of the front seat in the vehicle interior and a correlation value between the control sound from the left speaker 10L and the control sound from the right speaker 10R is calculated based on the recorded data. In this case, the left and right speakers 10L and 10R output the sine waves, the frequency of which is variously varied.

FIG. 3B shows an example of a relationship of the correlation value with respect to the phase difference (shown on a horizontal axis) and the frequency (shown on a vertical axis), which is obtained by the above record. A left direction on the horizontal axis indicates that the control sound from the left speaker 10L lags behind the control sound from the right speaker 10R in the phase. Aright direction on the horizontal axis indicates that the control sound from the right speaker 10R lags behind the control sound from the left speaker 10L in the phase. Additionally, the frequency shown on the vertical axis corresponds to an example of frequency (50 (Hz) to 150 (Hz)) at which the vibration noise of the engine should be actively controlled.

FIG. 3B shows that there is a basic tendency that the correlation value becomes higher (the correlation value becomes a value on an in-phase side) when the phase difference is close to 0 and the correlation value becomes lower (the correlation value becomes a value on a reverse phase side) when the phase difference becomes larger. However, it can be understood that there is not the above tendency at a frequency close to 108 (Hz). Concretely, it can be understood that a phase shift from 60 to 90 degrees (corresponding to an acoustic shift from 50 to 80 (cm)) occurs at the frequency close to 108 (Hz). It is thought that one of the reasons is that the control sound makes a detour due to the configuration on the front side in the vehicle interior.

Figure 4A:
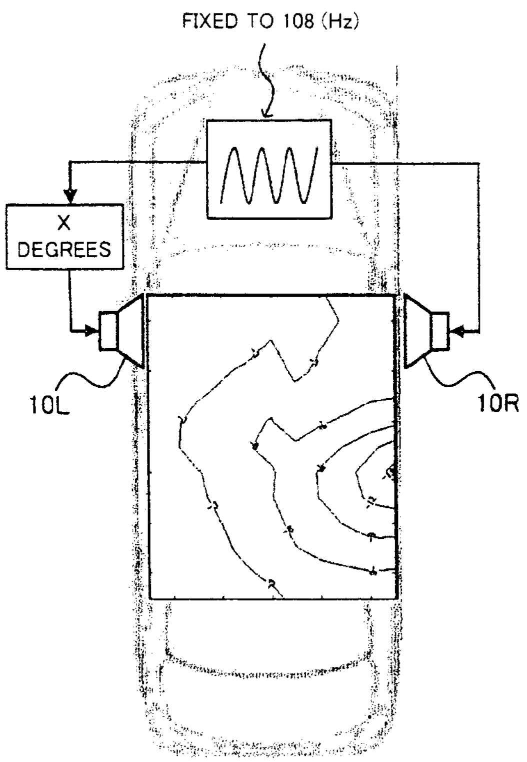
FIGS. 4A and 4B are diagrams for explaining a deviation of a sound pressure distribution.
Figure 4B:
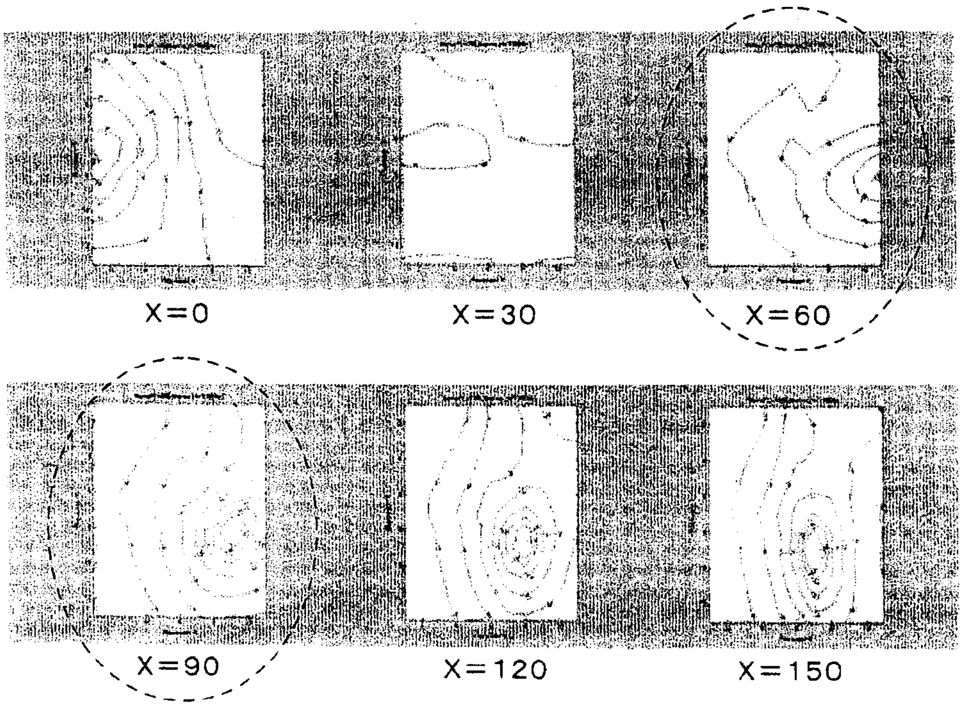

FIGS. 4A and 4B are diagrams for explaining a concrete example of a deviation of a sound pressure distribution. FIG. 4A shows the sound pressure distribution in the vehicle interior which is generated when the phase of the control sound from the speaker 10R is fixed and the phase of the control sound from the speaker 10L is shifted by "X degrees". In this case, it is assumed that the frequency of the control sounds from the speakers 10L and 10R is fixed to 108 (Hz) at which the large phase shift occurs as shown in FIG. 3B.

FIG. 4B shows examples of the sound pressure distribution in the vehicle interior which are obtained when the phase of the control sound from the speaker 10L is set to "X=0", "X=30", "X=60", "X=90", "X=120" and "X=150". As shown by broken lines in FIG. 4B, it can be understood that the un-uniform noise-cancelled area occurs at the rear seat when the phase is set to "X=60" and "X=90".

Here, the conventional active vibration noise control device repeatedly updates the filter coefficient used by the adaptive notch filter based on LMS (Least Mean Square) algorism so as to minimize the error signal at the microphone point, and provides the speakers 10L and 10R with the control signals which are processed by the updated filter coefficient. Therefore, in such a case that there is a phase difference between the speakers 10L and 10R, there is a tendency that the active vibration noise control device operates so that the acoustic distance of one of the control sounds becomes the same as the acoustic distance of the other based on the phase difference, at the time of canceling the engine noise which reaches the microphone from the front in the vehicle interior. Hence, at the frequency at which the large phase shift occurs, it is thought that the conventional active vibration noise control device generates the control signals used by the speakers 10L and 10R so that the phase difference between the control sounds becomes 60 to 90 degrees, for example. Namely, it is thought that the LMS excessively corrects the filter coefficient to the phase difference. As a result, it is thought that the un-uniform noise-cancelled area occurs at the rear seat as shown in FIG. 2. Namely, it is thought that the imbalance in the control sounds which reach the right and the left at the rear seat occurs.

Thus, in the embodiment, the active vibration noise control device adaptively limits the phase difference between the control sounds from the speakers 10L and 10R so as to appropriately suppress the occurrence of the un-uniform noise-cancelled area and ensure the wide noise-cancelled area. In other words, the active vibration noise control device adaptively limits output timing of sine waves from the speakers 10L and 10R.

Hereinafter, a description will be given of a concrete configuration which can appropriately limits the phase difference between the control sounds from the speakers 10L and 10R.

First Embodiment

In a first embodiment, the filter coefficient used by the adaptive notch filter is limited so as to limit the phase difference between the control sounds from the speakers 10L and 10R. Concretely, in the first embodiment, an angle on a two-dimensional plane between a filter coefficient (hereinafter referred to as "first filter coefficient") for generating the control signal of the speaker 10L and a filter coefficient (hereinafter referred to as "second filter coefficient") for generating the control signal of the speaker 10R is limited. Namely, an angular difference on the two-dimensional plane between the first filter coefficient and the second filter coefficient is limited to a predetermined angle or less. It is assumed that the first and second filter coefficients are represented by a two-dimensional vector.

Figure 5:
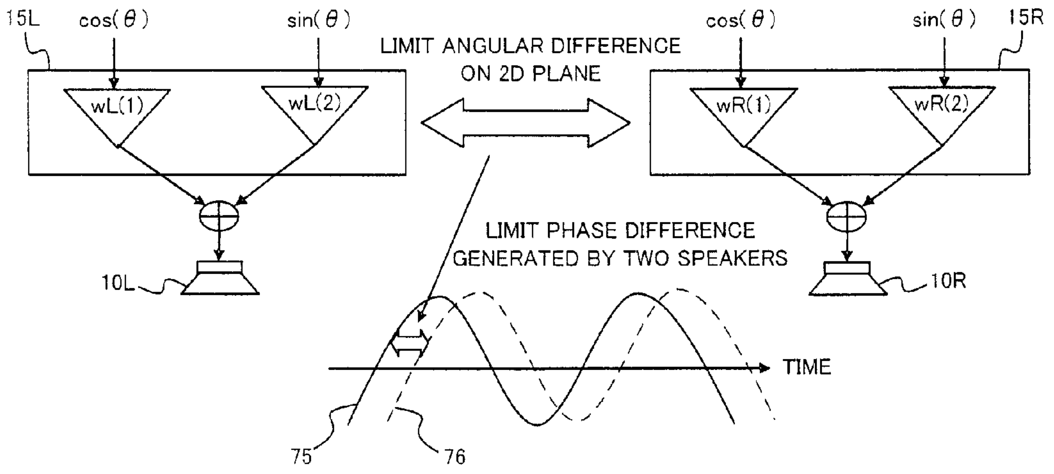
FIG. 5 is a diagram for explaining a basic concept of a control method in a first embodiment.

FIG. 5 is a diagram for explaining a basic concept of a control method in the first embodiment. As shown in FIG. 5, as for the active vibration noise control device, adaptive notch filters 15L and 15R perform filter processes of a cosine wave (cos (θ)) and a sine wave (sin (θ)), respectively. The active vibration noise control device adds a value obtained by the filter process of the adaptive notch filters 15L to a value obtained by the filter process of the adaptive notch filters 15R so as to generate the control signals. Then, the active vibration noise control device provides the control signals to the speakers 10L and 10R so as to generate the control sounds. In this case, the adaptive notch filter 15L performs the process by using the first filter coefficient defined by "wL(1)" and "wL(2)", and the adaptive notch filter 15R performs the process by using the second filter coefficient defined by "wR(1)" and "wR(2)".

By adding (i.e. combining) the cosine and sine waves after the filter processes, the control sounds (sine wave/cosine wave) having the phase difference are generated. As an example, the speaker 10L generates the control sound shown by a reference numeral 75, and the speaker 10R generates the control sound shown by a reference numeral 76.

In the first embodiment, the active vibration noise control device limits the angular difference on the two-dimensional plane between the first and second coefficients used by the adaptive notch filters 15L and 15R so as to adaptively limit the phase difference between the control sound from the speaker 10L and the control sound from the speaker 10R. Concretely, the active vibration noise control device performs the process so that the angular difference on the two-dimensional plane between the first and second coefficients becomes the predetermined angle or less.

Figure 6:
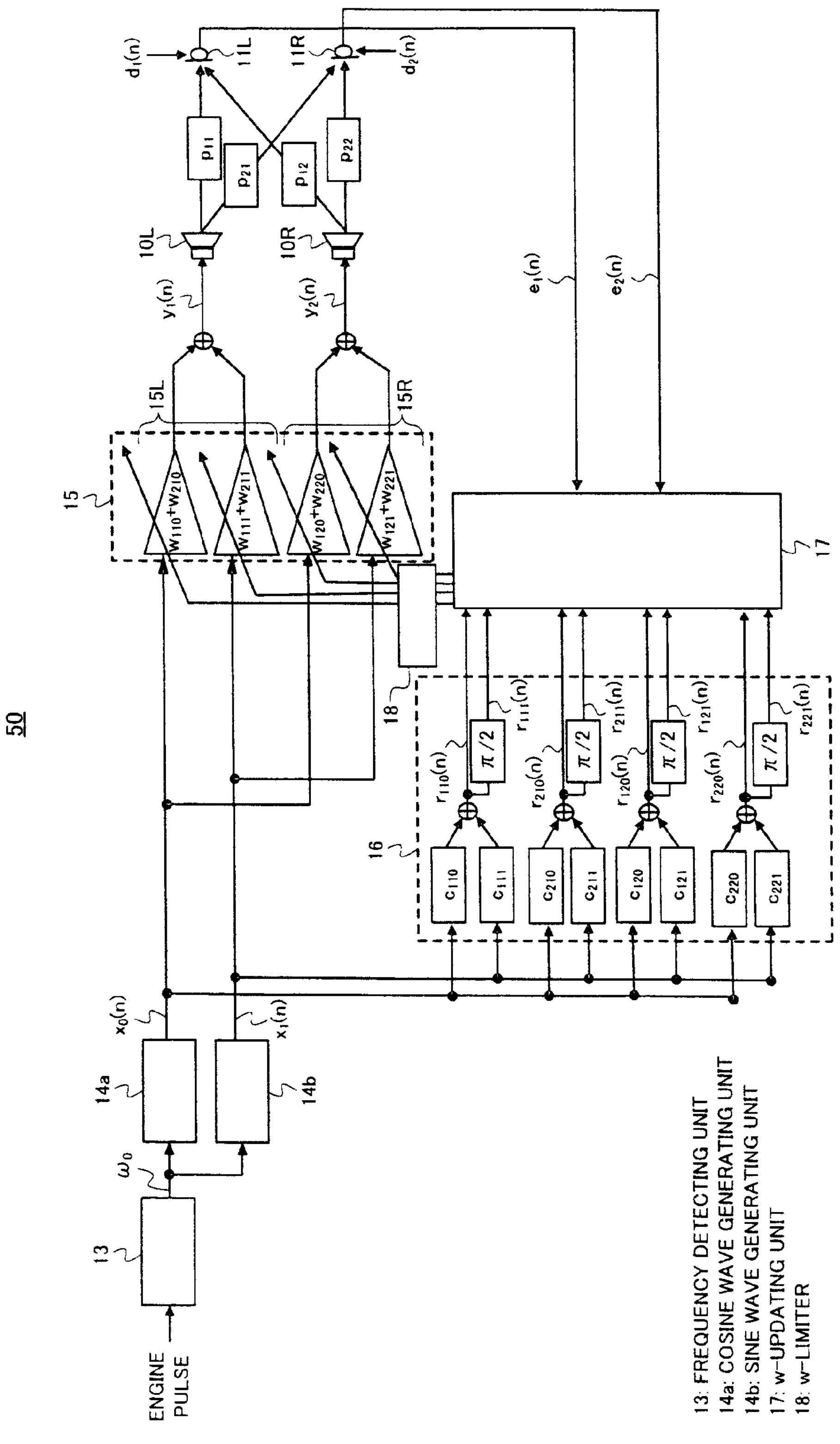
FIG. 6 shows a configuration of an active vibration noise control device in a first embodiment.

FIG. 6 shows a configuration of the active vibration noise control device 50 in the first embodiment. The active vibration noise control device 50 mainly includes two speakers 10L and 10R, two microphones 11L and 11R, a frequency detecting unit 13, a cosine wave generating unit 14*a*, a sine wave generating unit 14*b*, an adaptive notch filter 15, a reference signal generating unit 16, a w-updating unit 17 and a w-limiter 18.

Basically, the active vibration noise control device 50 actively controls the vibration noise generated by the engine by using a pair of speakers 10L and 10R and two microphones 11L and 11R. As shown in FIG. 1, the speakers 10L and 10R and the microphones 11L and 11R are installed on the front side in the vehicle interior (for example, the speakers 10L and 10R are installed in the front doors).

The frequency detecting unit 13 is provided with an engine pulse and detects a frequency $\omega_0$ of the engine pulse. Then, the frequency detecting unit 13 provides the cosine wave generating unit 14*a* and the sine wave generating unit 14*b* with a signal corresponding to the frequency $\omega_0$.

The cosine wave generating unit 14*a* and the sine wave generating unit 14*b* generate a basic cosine wave $x_0(n)$ and a basic sine wave $x_1(n)$ which include the frequency $\omega_0$ detected by the frequency detecting unit 13. Concretely, as shown by an equation (1), the basic cosine wave $x_0(n)$ and the basic sine wave $x_1(n)$ are generated. "n" is natural number and corresponds to time (The same will apply hereinafter). Additionally, in the equation (1), "A" indicates amplitude and "$\phi$" indicates an initial phase.

$$\left.\begin{aligned} x_0(n) &= A\cos(\omega_0 n + \phi) \\ x_1(n) &= A\sin(\omega_0 n + \phi) \end{aligned}\right\} \tag{1}$$

Then, the cosine wave generating unit 14*a* and the sine wave generating unit 14*b* provide the adaptive notch filter 15 and the reference signal generating unit 16 with basic signals corresponding to the basic cosine wave $x_0(n)$ and the basic sine wave $x_1(n)$. Thus, the cosine wave generating unit 14*a* and the sine wave generating unit 14*b* function as the basic signal generating unit.

The adaptive notch filter 15 performs the filter process of the basic cosine wave $x_0(n)$ and the basic sine wave $x_1(n)$ Concretely, the adaptive notch filter 15L multiplies the basic cosine wave $x_0(n)$ by "$w_{110}+w_{210}$" and multiplies the basic sine wave $x_1(n)$ by "$w_{111}+w_{211}$" so as to generate the control signal (hereinafter referred to as "first control signal") provided to the speaker 10L. The two values which are obtained by the multiplications are added up thereby to provide the speaker 10L with the first control signal $y_1(n)$. "$w_{110}+w_{210}$" and "$w_{111}+w_{211}$" are updated by the w-updating unit 17 which will be described later and are provided by the w-limiter 18. The above first filter coefficient is the two-dimensional vector defined by "$w_{110}+w_{210}$" and "$w_{111}+w_{211}$".

Meanwhile, the adaptive notch filter 15R multiplies the basic cosine wave $x_0(n)$ by "$w_{120}+w_{220}$" and multiplies the basic sine wave $x_1(n)$ by "$w_{121}+w_{221}$" so as to generate the control signal (hereinafter referred to as "second control signal") provided to the speaker 10R. The two values which are obtained by the multiplications are added up thereby to provide the speaker 10R with the second control signal $y_2(n)$. "$w_{120}+w_{220}$" and "$w_{121}+w_{221}$" are updated by the w-updating unit 17 which will be described later and are provided by the w-limiter 18. The above second filter coefficient is the two-dimensional vector defined by "$w_{120}$ $w_{220}$" and "$w_{121}+w_{221}$". Hereinafter, when the first and second filter coefficients are used with no distinction and the first and second filter coefficients are used together, the first and second filter coefficients are represented by "filter coefficient w".

For example, the first control signal $y_1(n)$ and the second control signal $y_2(n)$ are calculated by an equation (2). In the equation (2), "m" is 1 and 2, and "L" is 2.

$$\begin{aligned} y_m(n) &= \sum_{l=1}^{L} \{w_{lm0}(n)x_0(n) + w_{lm1}(n)x_1(n)\} \\ &= \sum_{l=1}^{L} \{w_{lm0}(n)A\cos(\omega_0 n + \phi) + w_{lm1}(n)A\sin(\omega_0 n + \phi)\} \end{aligned} \tag{2}$$

The speakers 10L and 10R generate the control sounds corresponding to the first control signal $y_1(n)$ and the second control signal $y_2(n)$, respectively. The control sounds are transferred in accordance with predetermined transfer functions in a sound field from the speakers 10L and 10R to the microphones 11L and 11R. Concretely, a transfer function from the speaker 10L to the microphone 11L is represented by "$p_{11}$", and a transfer function from the speaker 10L to the microphone 11R is represented by "$p_{21}$", and a transfer function from the speaker 10R to the microphone 11L is represented by "$p_{12}$", and a transfer function from the speaker 10R to the microphone 11R is represented by "$p_{22}$". The transfer functions $p_{11}$, $p_{21}$, $p_{12}$ and $p_{22}$ depend on the distance from the speakers 10L and 10R to the microphones 11L and 11R.

The microphones 11L and 11R detect the cancellation errors between the vibration noise of the engine and the control sounds from the speakers 10L and 10R, and provide the w-updating unit 17 with the cancellation errors as error signals $e_1(n)$ and $e_2(n)$. Concretely, the microphones 11L and 11R output the error signals $e_1(n)$ and $e_2(n)$ based on the first control signal $y_1(n)$, the second control signal $y_2(n)$, the transfer functions $p_{11}$, $p_{21}$, $p_{12}$ and $p_{22}$, the vibration noises $d_1(n)$ and $d_2(n)$ of the engine.

The reference signal generating unit 16 generates the reference signal from the basic cosine wave $x_0(n)$ and the basic sine wave $x_1(n)$ based on the above transfer functions $p_{11}$, $p_{21}$, $p_{12}$ and $p_{22}$, and provides the w-updating unit 17 with the reference signal. Concretely, the reference signal generating unit 16 uses a real part $C_{110}$ and an imaginary part $C_{111}$ of the transfer function $p_{11}$, a real part $C_{210}$ and an imaginary part $C_{211}$ of the transfer function $p_{21}$, a real part $C_{120}$ and an imaginary part $C_{121}$ of the transfer function $p_{12}$, a real part $C_{220}$ and an imaginary part $C_{221}$ of the transfer function $p_{22}$. In details, the reference signal generating unit 16 adds a value obtained by multiplying the basic cosine wave $x_0(n)$ by the real part $C_{110}$ of the transfer function $p_{11}$, to a value obtained by multiplying the basic sine wave $x_1(n)$ by the imaginary part $C_{111}$ of the transfer function $p_{11}$, and outputs a value obtained by the addition as the reference signal $r_{110}(n)$. In addition, the reference signal generating unit 16 delays the reference signal $r_{110}(n)$ by "$\pi/2$" and outputs the delayed signal as the reference signal $r_{111}(n)$. By a similar manner, the reference signal generating unit 16 outputs reference signals $r_{210}(n)$ $r_{211}(n)$, $r_{120}(n)$ $r_{121}(n)$ $r_{220}(n)$ and $r_{221}(n)$. Thus, the reference signal generating unit 16 functions as the reference signal generating unit.

The w-updating unit 17 updates the filter coefficient w used by the adaptive notch filter 15 based on the LMS algorism, and provides the w-limiter 18 with the updated filter coefficient w. Concretely, the w-updating unit 17 updates the filter coefficient w used by the adaptive notch filter 15 last time so as to minimize the error signals $e_1(n)$ and $e_2(n)$, based on the error signals $e_1(n)$ and $e_2(n)$, the reference signals $r_{110}(n)$, $r_{111}(n)$, $r_{210}(n)$ $r_{211}(n)$, $r_{120}(n)$, $r_{121}(n)$, $r_{220}(n)$ and $r_{221}(n)$. In details, the w-updating unit 17 multiplies a predetermined constant by the error signals $e_1(n)$ and $e_2(n)$ and the reference signals $r_{110}(n)$, $r_{111}(n)$, $r_{210}(n)$, $r_{211}(n)$, $r_{120}(n)$, $r_{121}(n)$, $r_{220}(n)$ and $r_{221}(n)$. Then, the w-updating unit 17 subtracts the value obtained by the multiplication from the filter coefficient w used by the adaptive notch filter 15 last time, and outputs the value obtained by the subtraction as a new filter coefficient w.

For example, the updated filter coefficient w is calculated by an equation (3). In the equation (3), the filter coefficient w after the update is represented by "$w_{lm0}(n+1)$" and "$w_{lm1}(n+1)$", and the filter coefficient w before the update is represented by "$w_{lm0}(n)$" and "$w_{lm1}(n)$". Additionally, in the equation (3), "α" is a predetermined constant called a step size for determining a convergence speed, and "l" is 1 and 2, and "m" is 1 and 2. "α" in the equation (3) is different from a limit angle which will be described later.

$$\left.\begin{aligned} w_{lm0}(n+1) &= w_{lm0}(n) - \alpha e_l(n) r_{lm0}(n) \\ w_{lm1}(n+1) &= w_{lm1}(n) - \alpha e_l(n) r_{lm1}(n) \end{aligned}\right\} \quad (3)$$

By the equation (3), the above $w_{110}$, $w_{111}$, $w_{120}$, $w_{121}$, $w_{210}$, $w_{211}$, $w_{220}$, $w_{221}$ are obtained. Then, the w-updating unit 17 provides the w-limiter 18 with "$w_{110}+w_{210}$", "$w_{111}+w_{211}$", "$w_{120}+w_{220}$" and "$w_{121}+w_{221}$" as the new filter coefficient w. Thus, the w-updating unit 17 functions as the filter coefficient updating unit.

The w-limiter 18 limits the filter coefficient w updated by the w-updating unit 17. Concretely, the limiter 18 limits the angular difference on the two-dimensional plane between the first filter coefficient (a two-dimensional vector defined by "$w_{110}$ $w_{210}$" and "$w_{111}+w_{211}$") and the second filter coefficient (a two-dimensional vector defined by "$w_{120}+w_{220}$" and "$w_{121}+w_{221}$"). Then, the w-limiter 18 provides the adaptive notch filter 15 with the filter coefficient w after the above limitation. Thus, the w-limiter 18 functions as the phase difference limiting unit.

Figure 7A:
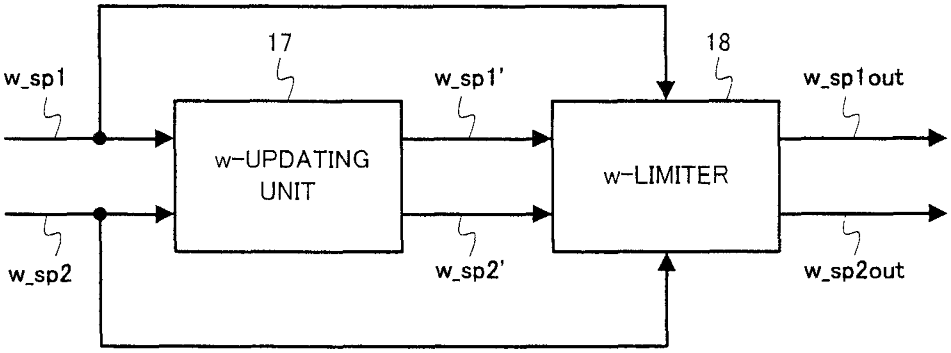
FIGS. 7A and 7B are diagrams for concretely explaining a process performed by a w-limiter.

Next, a description will be given of a concrete process performed by the w-limiter 18, with reference to FIGS. 7A and 7B. FIG. 7A is a schematic diagram showing process blocks of the w-updating unit 17 and the w-limiter 18. Here, the first and second filter coefficients before the update by the w-updating unit 17 are represented by "w_sp1" and "w_sp2", respectively. Additionally, the first and second filter coefficients after the update by the w-updating unit 17 are represented by "w_sp1" and "w_sp2", respectively.

The w-updating unit 17 updates the first filter coefficient w_sp1 for generating the first control signal of the speaker 10L and the second filter coefficient w_sp2 for generating the second control signal of the speaker 10R, based on the LMS algorism. Then, the w-updating unit 17 provides the w-limiter 18 with the updated first filter coefficient w_sp1' and the updated second filter coefficient w_sp2'. The w-limiter 18 outputs the first filter coefficient w_sp1_out and the second filter coefficient w_sp2_out finally used by the adaptive notch filters 15L and 15R, based on the first and second filter coefficients w_sp1' and w_sp2' after the update by the w-updating unit 17 and the first and second filter coefficients w_sp1 and w_sp2 before the update.

Figure 7B:
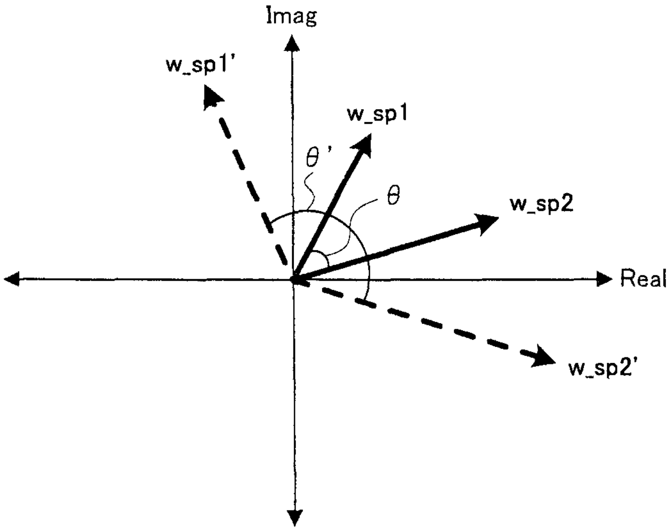

FIG. 7B is a diagram for concretely explaining a process performed by the w-limiter 18. In FIG. 7B, a horizontal axis shows a real axis, and a vertical axis shows an imaginary axis. Since the first filter coefficients w_sp1 and w_sp1' and the second filter coefficients w_sp2 and w_sp2' are represented by the two-dimensional vector defined by the real part and the imaginary part, these are represented as shown in FIG. 7B, for example. An angular difference on the two-dimensional plane between the first and second filter coefficients w_sp1 and w_sp2 before the update is defined as "θ", and an angular difference on the two-dimensional plane between the first and second filter coefficients w_sp1' and w_sp2' after the update is defined as "θ'".

In the first embodiment, the w-limiter 18 limits the angular difference between the first and second filter coefficients w_sp1_out and w_sp2_out which are finally used by the adaptive notch filter 15, to the predetermined angle (hereinafter referred to as "limit angle α") or less. The limit angle α is set based on such a range that the deviation of the sound pressure distribution generated by the speakers 10L and 10R does not occur. For example, the limit angle α is calculated by an experiment and/or a predetermined calculating formula for each vehicle. As an example, the limit angle α is set to "30 degrees" at which the sound pressure distribution becomes uniform as shown in FIG. 4B.

Concretely, when the angular difference θ' between the first and second filter coefficients w_sp1' and w_sp2' after the update by the w-updating unit 17 is lager than the limit angle α, the w-limiter 18 outputs the first and second filter coefficients w_sp1 and w_sp2 before the update, as the first and second filter coefficients w_sp1_out and w_sp2_out. Namely, the w-limiter 18 does not update the filter coefficient used by the adaptive notch filter 15. In other words, the filter coefficient used by the adaptive notch filter 15 last time is used once again.

In contrast, when the angular difference θ' is equal to or smaller than the limit angle α, the w-limiter 18 outputs the first and second filter coefficients w_sp1' and w_sp2' after the update, as the first and second filter coefficients w_sp1_out and w_sp2_out. Namely, the w-limiter 18 updates the filter coefficient used by the adaptive notch filter 15. When norm of the first coefficient w_sp1' is "0" (i.e. "|w_sp1'|=0") or norm of the second coefficient w_sp2' is "0" (i.e. "|w_sp2'|=0"), the w-limiter 18 outputs the first and second filter coefficients w_sp1' and w_sp2' after the update, as the first and second filter coefficients w_sp1_out and w_sp2_out, too. This is because the angular difference between the first and second filter coefficients w_sp1' and w_sp2' cannot be defined.

It is not limited that the w-limiter 18 determines whether to output the first and second filter coefficients w_sp1' and w_sp2' after the update or the first and second filter coefficients w_sp1 and w_sp2 before the update, based on the angular difference θ' between the first and second filter coefficients w_sp1' and w_sp2', the norm of the first coefficient w_sp1' and the norm of the second coefficient w_sp2'. As another example, such a determination can be performed based on "X" defined by an equation (4) and "Y" defined by an equation (5). "|·|" in the equation (4) indicates norm of the vector, and "<·>" in the equation (5) indicates inner product of the vector.

$$X = |w\_sp1'| \cdot |w\_sp2| \quad (4)$$

$$Y = \langle w\_sp1', w\_sp2' \rangle \quad (5)$$

When "X" and "Y" are used, the w-limiter 18 determines whether or not such a condition (hereinafter referred to as "first condition") that "$X^2 \neq 0$" and "$Y \geq 0$" and "$Y^2 \geq X^2 (\cos\alpha)^2$" is satisfied or determines whether or not such a condition (hereinafter referred to as "second condition") that "$X^2=0$" is satisfied, so as to determine whether to output the first and second filter coefficients w_sp1' and w_sp2' or the first and second filter coefficients w_sp1 and w_sp2.

Concretely, when the first condition is satisfied, or when the second condition is satisfied, the w-limiter 18 outputs the first and second filter coefficients w_sp1' and w_sp2' after the update, as the first and second filter coefficients w_sp1_out and w_sp2_out. In contrast, when the first condition is not satisfied and the second condition is not satisfied, the w-limiter 18 outputs the first and second filter coefficients w_sp1 and w_sp2 before the update, as the first and second filter coefficients w_sp1_out and w_sp2_out.

When the determination is performed by using "X" and "Y", it becomes possible to perform the determination more easily than when the determination is performed based on the angular difference θ', the norm of the first coefficient w_sp1' and the norm of the second coefficient w_sp2'.

Figure 8:
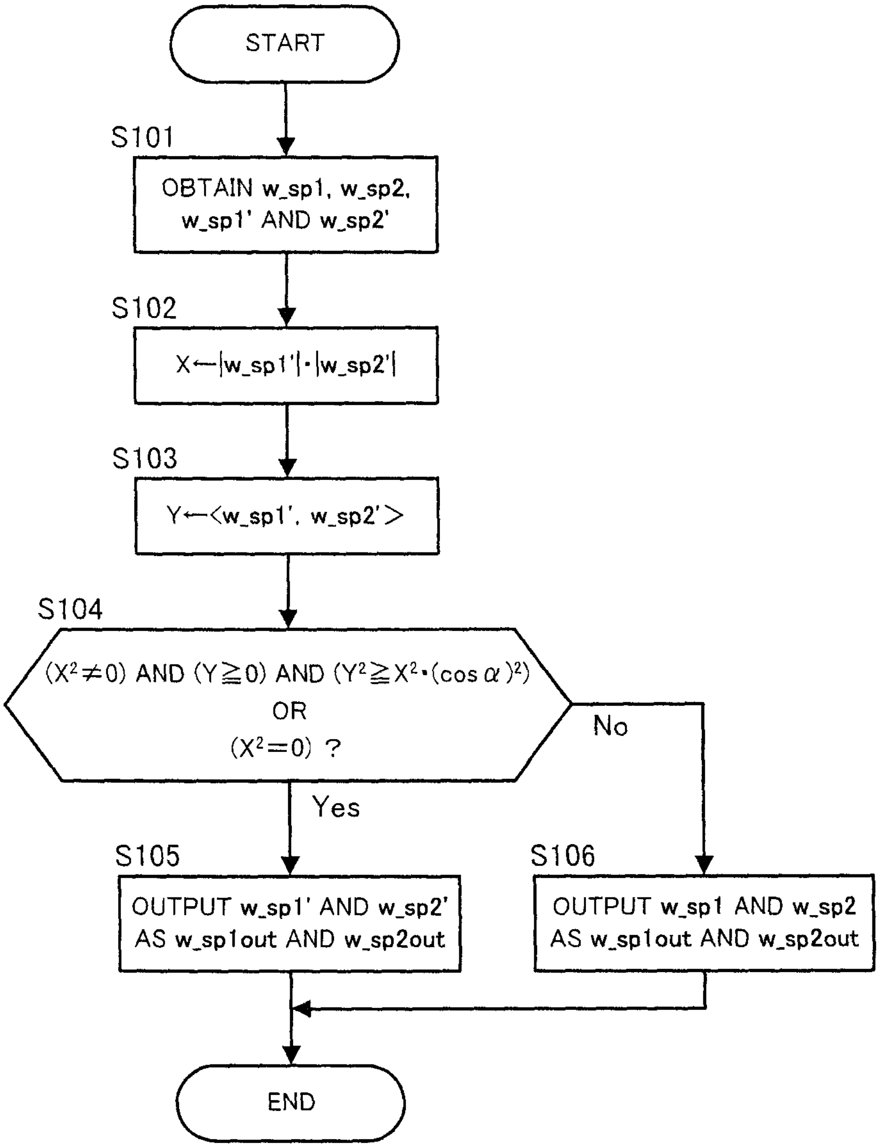
FIG. 8 is a flow chart showing a process performed by a w-limiter.

Next, a description will be given of a concrete example of the process performed by the w-limiter 18, with reference to FIG. 8. FIG. 8 is a flow chart showing the process performed by the w-limiter 18.

First, in step S101, the w-limiter 18 obtains the first and second filter coefficients w_sp1 and w_sp2 before the update by the w-updating unit 17 and the first and second filter coefficients w_sp1' and w_sp2' after the update by the w-updating unit 17. Then, the process goes to step S102.

In step S102, the w-limiter 18 calculates "X" by using the above equation (4), based on the values obtained in step S101. Then, the process goes to step S103. In step S103, the w-limiter 18 calculates "Y" by using the above equation (5), based on the values obtained in step S101. Then, the process goes to step S104.

In step S104, by using "X" and "Y" obtained in steps S102 and S103, the w-limiter 18 determines whether or not the first condition or the second condition is satisfied. In step S104, basically, the w-limiter 18 determines whether or not the angular difference θ' between the first and second coefficients w_sp1' and w_sp2' after the update by the w-updating unit 17 is equal to or smaller than the limit angle α, in order to limit the angular difference between the first and second coefficients w_sp1_out and w_sp2_out finally used by the adaptive notch filter 15, to the limit angle α or less.

When the first condition is satisfied or the second condition is satisfied (step S104: Yes), the process goes to step S105. In this case, the w-limiter 18 outputs the first and second filter coefficients w_sp1' and w_sp2' after the update, as the first and second filter coefficients w_sp1_out and w_sp2_out. Then, the process ends.

Meanwhile, when the first condition is not satisfied and the second condition is not satisfied (step S104: No), the process goes to step S106. In this case, the w-limiter 18 outputs the first and second filter coefficients w_sp1 and w_sp2 before the update, as the first and second filter coefficients w_sp1_out and w_sp2_out. Then, the process ends.

Next, a description will be given of an effect of the active vibration noise control device 50 in the first embodiment, with reference to FIGS. 9A and 9B. Here, a description will be given of the sound pressure distribution (in other words, noise-cancelled amount for each area) which is obtained when the speakers 10L and 10R and the microphones 11L and 11R are installed in the vehicle interior as shown in FIG. 1 and the speakers 10L and 10R generate the control sounds so as to actively control the vibration noise of the engine. In this case, it is assumed that the frequency of the control sounds from the speakers 10L and 10R is fixed to 108 (Hz) at which the large phase shift occurs as shown in FIG. 3B. Additionally, a result obtained by the conventional active vibration noise control device is shown for a comparison. It is assumed that the conventional active vibration noise control device does not limit the filter coefficient w by the w-limiter 18 like the active vibration noise control device 50.

Figure 9A:
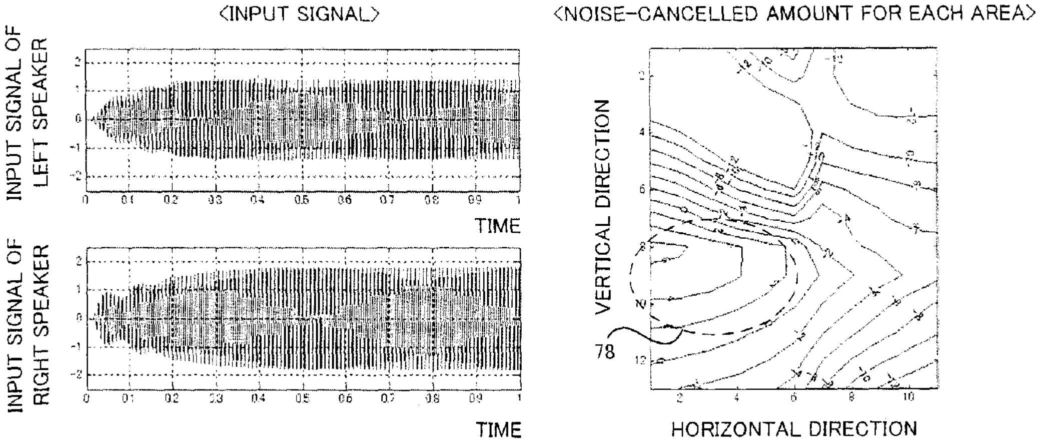
FIGS. 9A and 9B are diagrams for explaining an effect of an active vibration noise control device in a first embodiment.

FIG. 9A shows an example of a result by the conventional active vibration noise control device. A left graph in FIG. 9A shows input signals (corresponding to $y_1(n)$ and $y_2(n)$) of the speakers 10L and 10R, and a right graph in FIG. 9A shows noise-cancelled amount (dB) for each area in the vehicle interior. As shown in FIG. 9A, according to the conventional active vibration noise control device, it can be understood that the vibration noise increases at the position of the left rear seat as shown by an area drawn in a broken line 78 and the un-uniform noise-cancelled area occurs. This is caused by the above-mentioned reason. Namely, this is because, since the LMS corrects the phase difference at the front seat as shown in FIG. 3A, the sound pressure distribution by the control signals deviates at the rear seat as shown in FIG. 4B. Additionally, it can be understood that the amplitudes of the input signals of the speakers 10L and 10R are relatively large. This is because, since the error obtained by the microphone does not decrease due to the occurrence of the area drawn in the broken line 78, the amplitude of the filter coefficient continues to increase.

Figure 9B:
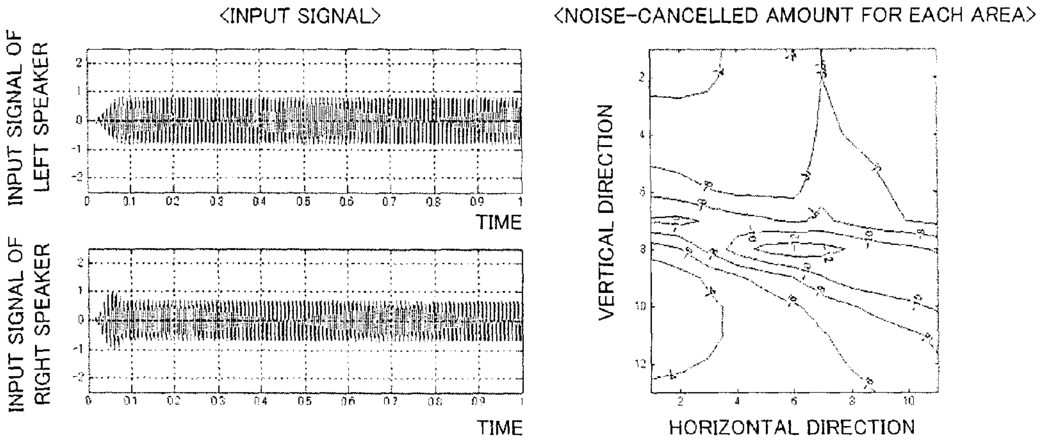

FIG. 9B shows an example of a result by the active vibration noise control device 50 in the first embodiment. A left graph in FIG. 9B shows input signals (corresponding to $y_1(n)$ and $y_2(n)$) of the speakers 10L and 10R, and a right graph in FIG. 9B shows noise-cancelled amount (dB) for each area in the vehicle interior. As shown in FIG. 9B, according to the active vibration noise control device 50 in the first embodiment, it can be understood that an uniform and wide noise-cancelled area is ensured. Concretely, it can be understood that the occurrence of the un-uniform noise-cancelled area as shown in FIG. 9A is suppressed. Additionally, it can be understood that the amplitudes of the input signals of the speakers 10L and 10R are smaller than that of the input signals by the conventional active vibration noise control device. This is because the active vibration noise control device 50 in the first embodiment limits the update of the filter coefficient w by using the w-limiter 18.

Thus, by the active vibration noise control device 50 in the first embodiment, it becomes possible to appropriately ensure the uniform and wide noise-cancelled area by the relatively small volume of the control sounds. Therefore, it becomes possible to ensure the wide noise-cancelled area by a few microphones.

Second Embodiment

Next, a description will be given of a second embodiment. The second embodiment is different from the first embodiment in that a phase difference between the first control signal provided to the speaker 10L and the second control signal provided to the speaker 10R is directly limited so as to limit the phase difference between the control sounds from the speakers 10L and 10R. Concretely, in the second embodiment, the phase difference between the first control signal and the second control signal is limited to a predetermined value or less.

Figure 10:
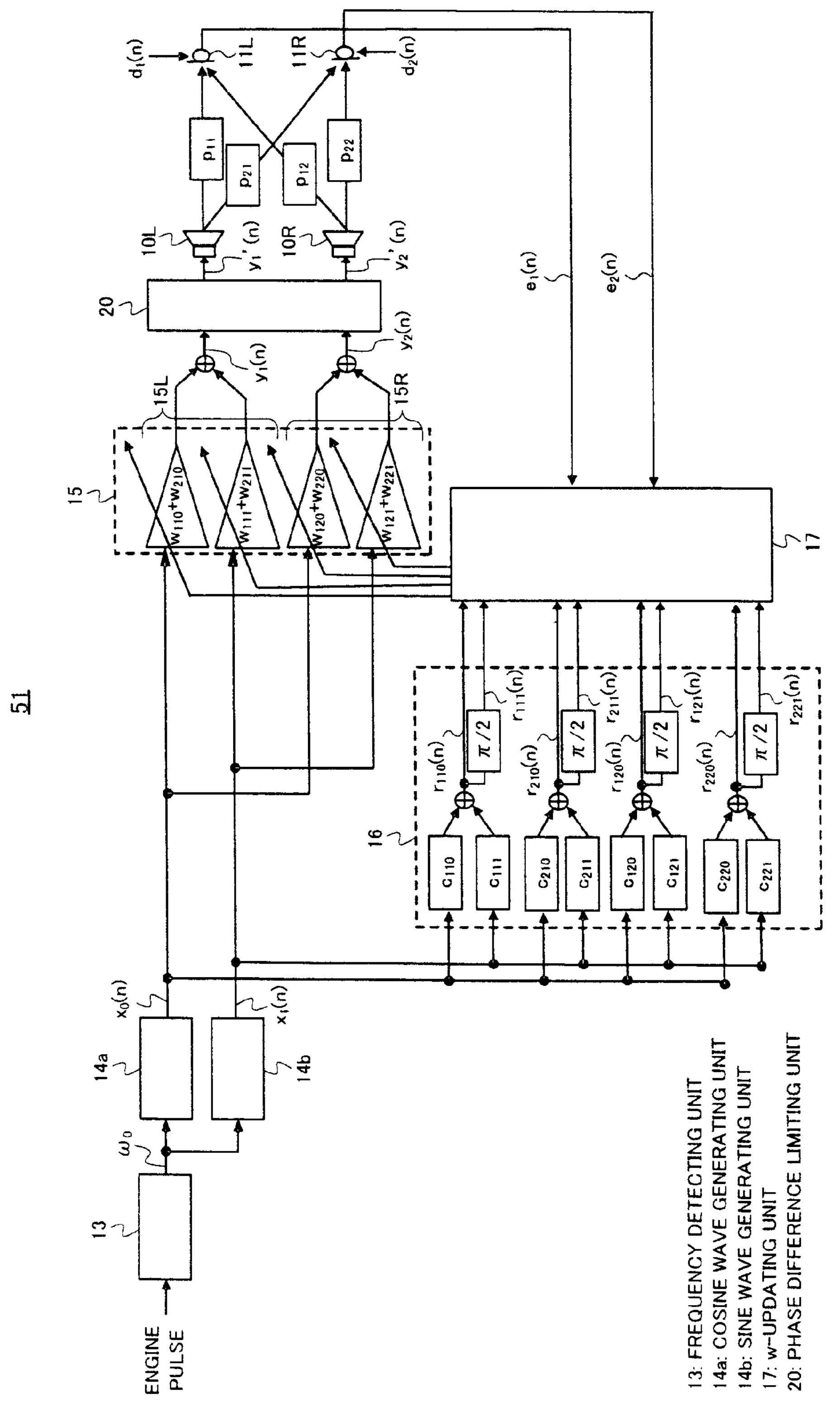
FIG. 10 shows a configuration of an active vibration noise control device in a second embodiment.

FIG. 10 shows a configuration of the active vibration noise control device 51 in the second embodiment. The active vibration noise control device 51 is different from the active vibration noise control device 50 (see FIG. 6) in that a phase difference limiting unit 20 instead of the w-limiter 18 is included. The same reference numerals are given to the same components as those of the active vibration noise control device 50, and explanations thereof are omitted.

The phase difference limiting unit 20 includes a buffer. The phase difference limiting unit 20 is provided with the first control signal $y_1(n)$ and the second control signal $y_2(n)$ after the process of the adaptive notch filter 15 and limits the phase difference between the first control signal $y_1(n)$ and the second control signal $y_2(n)$. Concretely, the phase difference limiting unit 20 limits the phase difference between the first and second control signals $y_1(n)$ and $y_2(n)$, to the predetermined value or less. For example, when the phase difference is larger than the predetermined value, the phase difference limiting unit 20 delays one of the first and second control signals $y_1(n)$ and $y_2(n)$, the phase of which is more advanced than that of the other, by amount corresponding to a difference between the phase difference and the predetermined value. Then, the phase difference limiting unit 20 provides the speakers 10L and 10R with a first control signal $y_1'(n)$ and a second control signal $y_2'(n)$ after the above process. Thus, the phase difference limiting unit 20 functions as the phase difference limiting unit.

Figure 11:
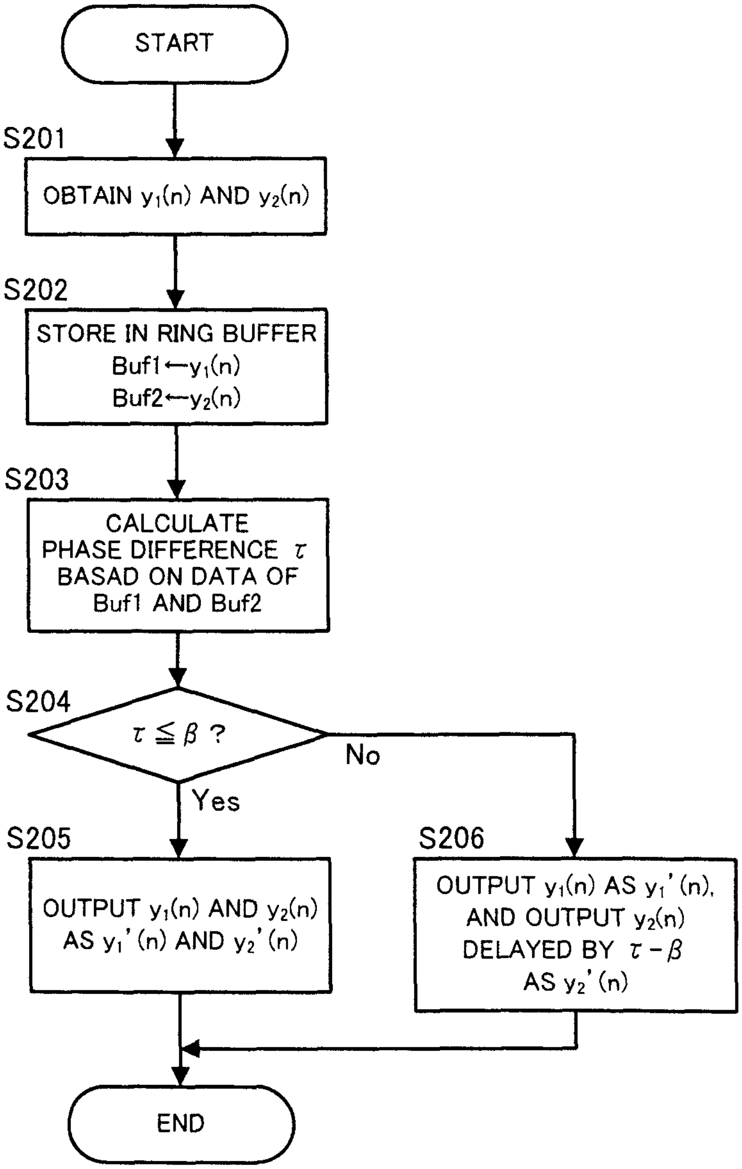
FIG. 11 is a flow chart showing a process performed by a phase difference limiting unit.

Next, a description will be given of a concrete example of the process performed by the phase difference limiting unit 20, with reference to FIG. 11. FIG. 11 is a flow chart showing the process performed by the phase difference limiting unit 20. Here, a description will be given of an example in such a case that the phase of the first control signal $y_1(n)$ is less advanced than that of the second control signal $y_2(n)$ (in other words, the phase of the second control signal $y_2(n)$ is more advanced than that of the first control signal $y_1(n)$).

First, in step S201, the phase difference limiting unit 20 obtains the first control signal $y_1(n)$ and the second control signal $y_2(n)$. Then, the process goes to step S202.

In step 202, the phase difference limiting unit 20 stores the first and second control signals $y_1(n)$ and $y_2(n)$ obtained in step S201, in a ring buffer. Concretely, the phase difference limiting unit 20 stores the first control signal $y_1(n)$ in a buffer Buf1 and stores the second control signal $y_2(n)$ in a buffer Buf2. For example, the phase difference limiting unit 20 stores data corresponding to about one wavelength of the sine wave, in the buffers Buf1 and Bu2. This is because the phase difference is calculated by using a shape of the sine wave. Then, the process goes to step S203.

In step S203, the phase difference limiting unit 20 calculates a phase difference t between the first and second control signals $y_1(n)$ and $y_2(n)$, based on the data stored in the buffers Buf1 and Buf2. Concretely, the phase difference limiting unit 20 calculates a correlation value of the data stored in the buffers Buf1 and Buf2 (for example, calculates the inner product), so as to calculate the phase difference $\tau$. In this case, the phase difference limiting unit 20 calculates the correlation value while shifting time of the data stored in the buffers Buf1 and Buf2, and adopts the time at which a peak value of the correlation value is obtained, as the phase difference $\tau$. Then, the process goes to step S204.

In step S204, the phase difference limiting unit 20 determines whether or not the phase difference $\tau$ obtained in step S203 is equal to or smaller than the predetermined value $\beta$. The predetermined value $\beta$ is set based on such a range that the deviation of the sound pressure distribution generated by the speakers 10L and 10R does not occur. For example, the predetermined value $\beta$ is calculated by an experiment and/or a predetermined calculating formula for each vehicle.

When the phase difference $\tau$ is equal to or smaller than the predetermined value $\beta$ (step S204: Yes), the process goes to step S205. In step S205, since it is not necessary to limit the phase difference between the first and second control signals $y_1(n)$ and $y_2(n)$, the phase difference limiting unit 20 outputs the original first and second control signals $y_1(n)$ and $y_2(n)$, as the first and second control signals $y_1'(n)$ and $y_2'(n)$. Then, the process ends.

In contrast, when the phase difference $\tau$ is larger than the predetermined value $\beta$ (step S204: No), the process goes to step S206. In step S206, the phase difference limiting unit 20 limits the phase difference between the first and second control signals $y_1(n)$ and $y_2(n)$. Concretely, the phase difference limiting unit 20 delays the second control signal $y_2(n)$ which is advanced in the phase, by the amount "$\tau-\beta$" corresponding to the difference between the phase difference $\tau$ and the predetermined value $\beta$. Then, the phase difference limiting unit 20 outputs the original first control signal $y_1(n)$ as the first control signal $y_1'$, and outputs the second control signal $y_2(n)$ delayed by "$\tau-\beta$", as the second control signal $y_2'(n)$. Then, the process ends. Meanwhile, when the phase of the first control signal $y_1(n)$ is more advanced than that of the second control signal $y_2(n)$, the phase difference limiting unit 20 outputs the first control signal $y_1(n)$ delayed by "$\tau-\beta$", as the first control signal $y_1'(n)$.

By the above active vibration noise control device 51 in the second embodiment, it becomes possible to appropriately ensure the uniform and wide noise-cancelled area by the relatively small volume of the control sounds.

The above second, embodiment shows such an example that the phase difference limiting unit 20 delays one of the first and second control signals $y_1(n)$ and $y_2(n)$, the phase of which is more advanced than that of the other, by "$\tau-\beta$". Instead of this, the phase difference limiting unit 20 may advance one of the first and second control signals $y_1(n)$ and $y_2(n)$, the phase of which is less advanced than that of the other, by "$\tau-\beta$".

[Modification]

While the above embodiments show such an example that the active vibration noise control device is formed by using a pair of speakers, it is not limited to this. As another example, the active vibration noise control device can be formed by using more than one pair of speakers. For example, the active vibration noise control device can be formed by using a total of four speakers or a total of six speakers. In this case, by a similar method as the above-mentioned method, the control signals may be generated for each pair of speakers.

Additionally, while the above embodiments show such an example that the active vibration noise control device is formed by using two microphones, it is not limited to this. The active vibration noise control device may be formed by using one microphone or more than two microphones.

Additionally, it is not limited that the present invention is applied to the vehicle. Other than the vehicle, the present invention can be applied to various kinds of transportation such as a ship or a helicopter or an airplane.

INDUSTRIAL APPLICABILITY

This invention is applied to closed spaces such as an interior of transportation having a vibration noise source (for example, engine), and can be used for actively controlling a vibration noise.

DESCRIPTION OF REFERENCE NUMBERS

10L, 10R Speaker
11L, 11R Microphone
13 Frequency Detecting Unit
14*a* Cosine Wave Generating Unit
14*b* Sine Wave Generating Unit
15 Adaptive Notch Filter
16 Reference Signal Generating Unit
17 w-Updating Unit
18 w-Limiter
20 Phase Difference Limiting Unit
50, 51 Active Vibration Noise Control Device

The invention claimed is:

1. An active vibration noise control device having a pair of speakers which makes the speakers generate control sounds, comprising:

a basic signal generating unit which generates a basic signal based on a vibration noise frequency generated by a vibration noise source;

an adaptive notch filter which generates a first control signal provided to one of the speakers by applying a first filter coefficient to the basic signal and generates a second control signal provided to the other speaker by applying a second filter coefficient to the basic signal, in order to make the speakers generate the control sounds so that the vibration noise generated by the vibration noise source is cancelled;

a microphone which detects a cancellation error between the vibration noise and the control sounds, and outputs an error signal;

a reference signal generating unit which generates a reference signal from the basic signal based on a transfer function from the speakers to the microphone;

a filter coefficient updating unit which updates the first and second filter coefficients used by the adaptive notch filter based on the error signal and the reference signal so as to minimize the error signal; and a phase difference limiting unit which limits a phase difference between a control sound generated by one of the speakers and a control sound generated by the other speaker.

2. The active vibration noise control device according to claim 1, wherein the phase difference limiting unit limits the phase difference so that a sound pressure distribution generated by the control sounds from the speakers becomes uniform.

3. The active vibration noise control device according to claim 1, wherein the phase difference limiting unit limits an angular difference on a two-dimensional plane between the first and second filter coefficients updated by the filter coefficient updating unit, to a predetermined angle or less, so as to limit the phase difference between the control sound generated by one of the speakers and the control sound generated by the other speaker.

4. The active vibration noise control device according to claim 3, wherein, when the angular difference is larger than the predetermined angle, the phase difference limiting unit provides the adaptive notch filter with the first and second filter coefficients before the update by the filter coefficient updating unit.

5. The active vibration noise control device according to claim 1, wherein the phase difference limiting unit limits a phase difference between the first and second control signals generated by the adaptive notch filter, to a predetermined value or less, so as to limit the phase difference between the control sound generated by one of the speakers and the control sound generated by the other speaker.

6. The active vibration noise control device according to claim 5, wherein, when the phase difference is larger than the predetermined value, the phase difference limiting unit delays one of the first and second control signals, a phase of which is more advanced than that of the other, by amount corresponding to a difference between the phase difference and the predetermined value.

7. The active vibration noise control device according to claim 1, wherein the speakers are arranged close to the vibration noise source.

* * * * *